United States Patent [19]

Eguchi et al.

[11] Patent Number: 4,527,564

[45] Date of Patent: Jul. 9, 1985

[54] SUTURING NEEDLE FOR MEDICAL OPERATION

[75] Inventors: Yasukata Eguchi, Tokyo; Reishi Nomoto; Masayoshi Takahashi, both of Kanagawa, all of Japan

[73] Assignee: Janome Sewing Machine Co. Ltd., Japan

[21] Appl. No.: 230,581

[22] Filed: Feb. 2, 1981

[30] Foreign Application Priority Data

Feb. 6, 1980 [JP] Japan .............................. 55-12813[U]
May 23, 1980 [JP] Japan .............................. 55-70263[U]

[51] Int. Cl.³ ............................................ A61B 17/06
[52] U.S. Cl. ....................................................... 128/339
[58] Field of Search ................ 128/339, 340; 223/104; 112/169

[56] References Cited

U.S. PATENT DOCUMENTS 2,336,689 12/1943 Karle .................................... 128/339

Primary Examiner—Michael H. Thaler
Attorney, Agent, or Firm—Michael J. Striker

[57] ABSTRACT

A curved needle for use in medical operations includes a grip to be mounted in a suturing machine and a curved portion terminated with a needle eye for receiving a needle. On the outside of the curved portion an elongated groove is formed for guiding a thread toward the needle eye. The groove includes a partially closed portion for preventing the thread from slipping out from the groove.

5 Claims, 24 Drawing Figures

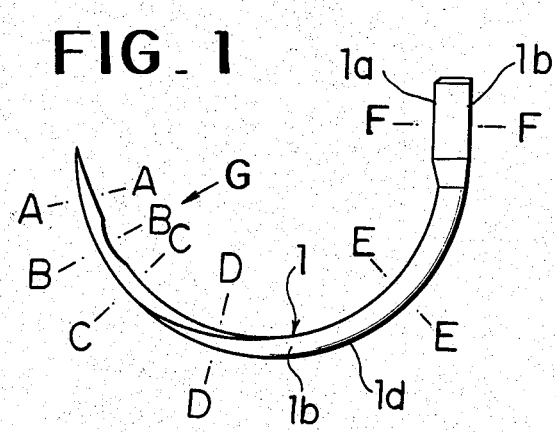
FIG_1
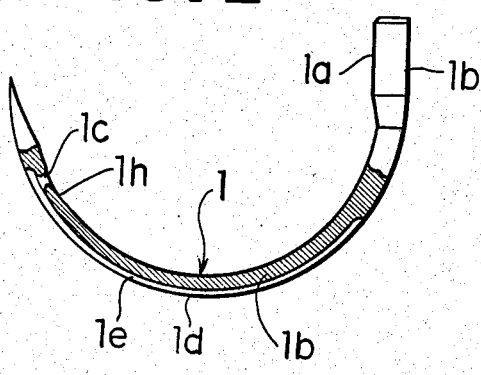
FIG_2
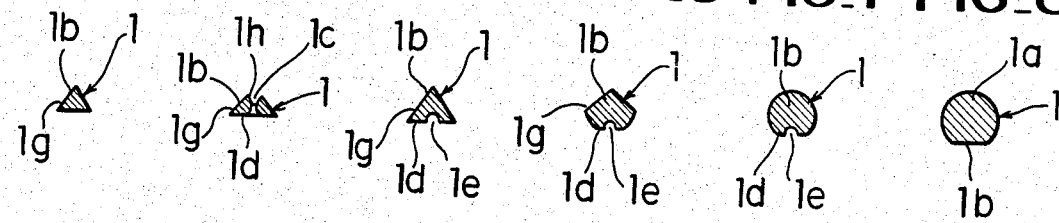
FIG_3 FIG_4 FIG_5 FIG_6 FIG_7 FIG_8
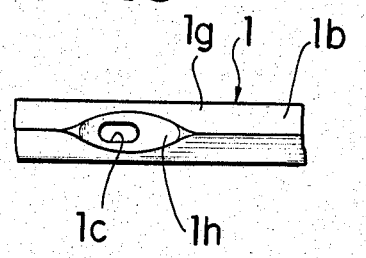
FIG_9
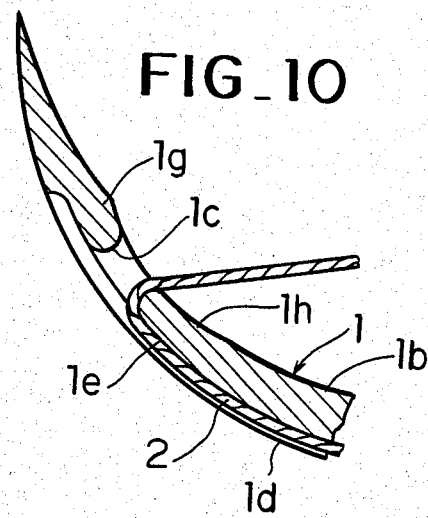
FIG_10

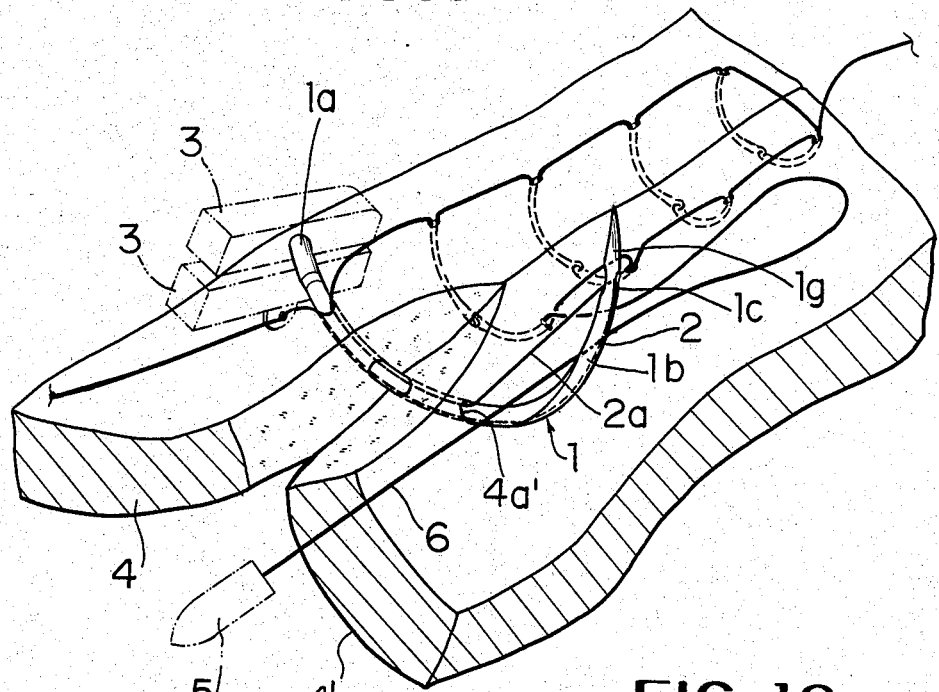
FIG_11
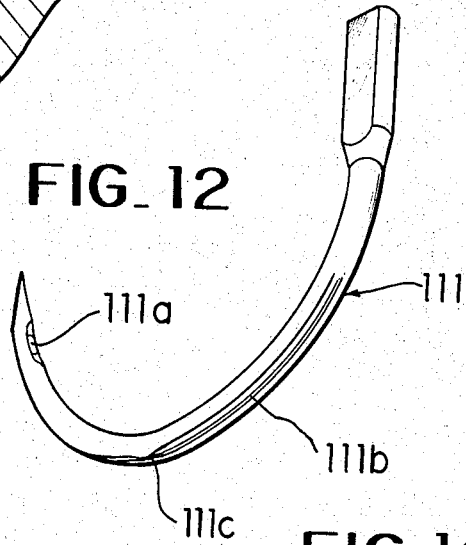
FIG_12
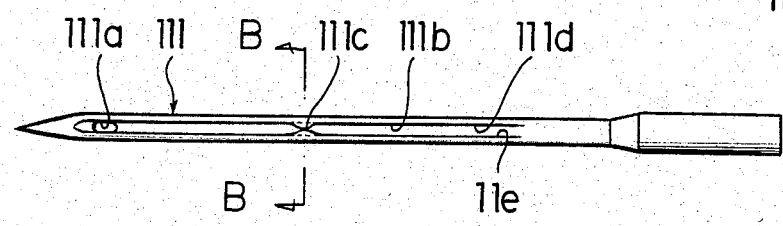
FIG_13
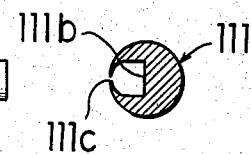
FIG_14
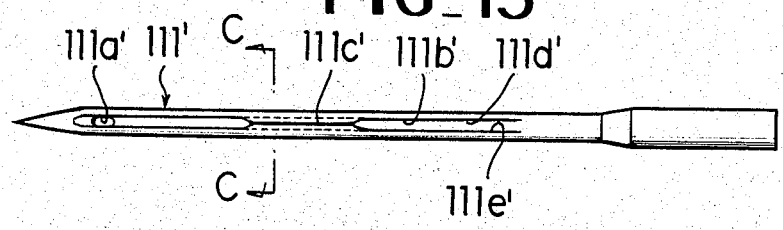
FIG_15
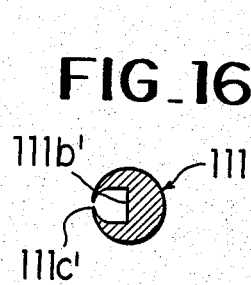
FIG_16

FIG_17
FIG_18
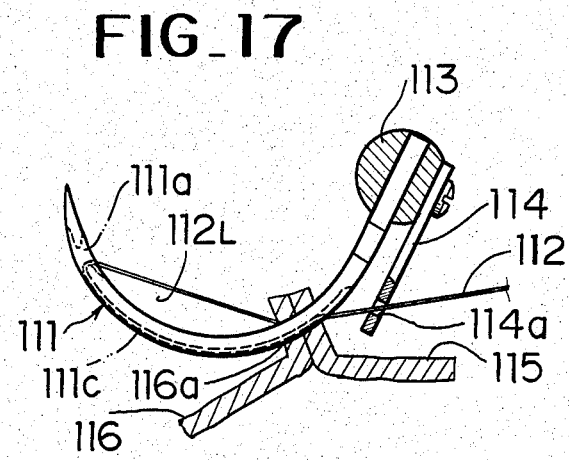
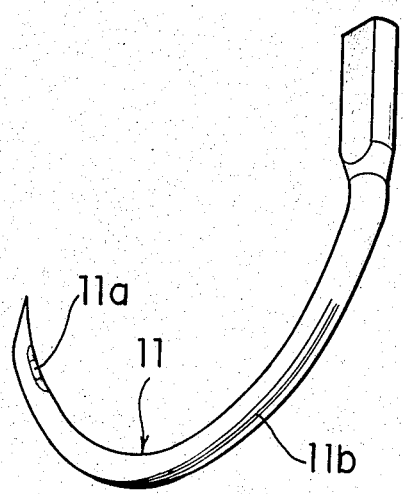
FIG_19
FIG_20
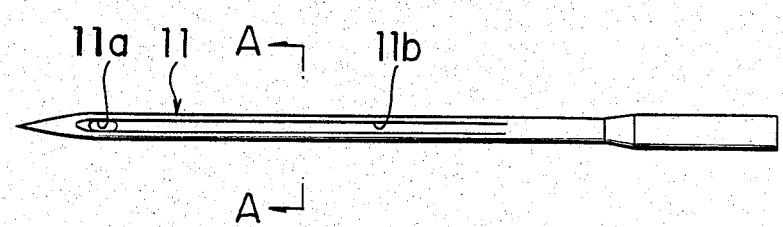
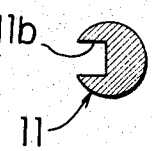
FIG_21
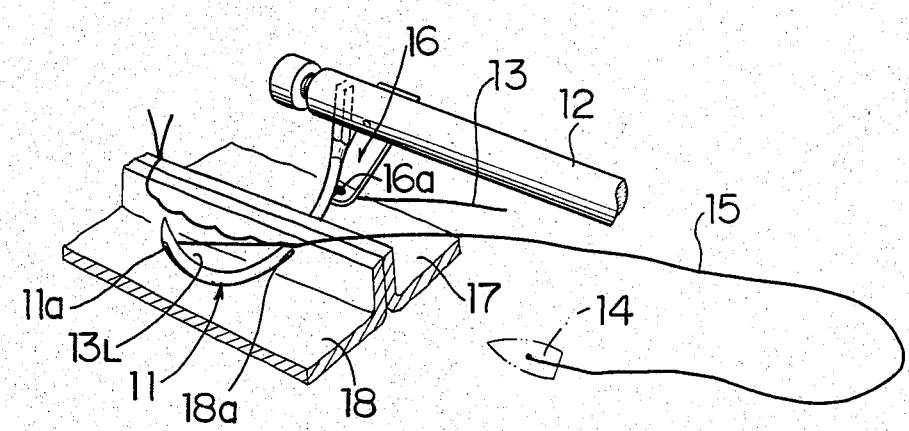

FIG_22
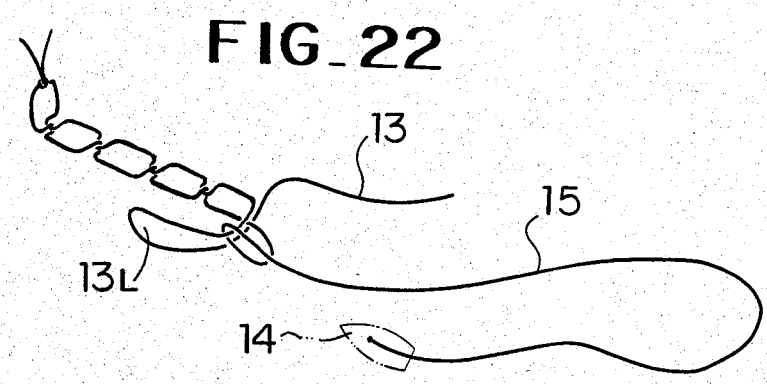
FIG_23
FIG_24
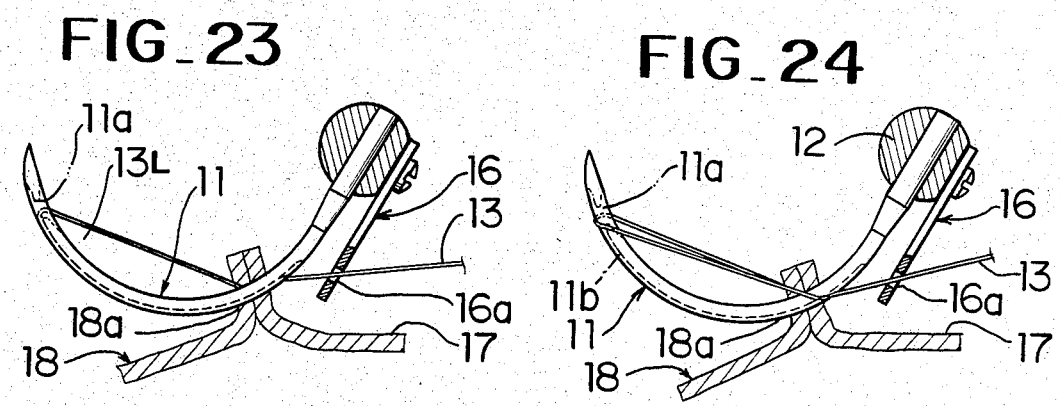

SUTURING NEEDLE FOR MEDICAL OPERATION

BACKGROUND OF THE INVENTION

The present invention relates to a suturing needle for medical operation, which is especially to be used to a medical suturing device for human parts to be sutured up in a lock stitching manner without changing in holding the needle.

It has been a conventional practice to carry out the suturing operation at the incised parts of a patient by a curved needle formed with a needle eye at the shank thereof, which is held by a holder handled by an operator with a thread passed through the needle eye of the curved needle. Thus, the curved needle is inserted into a part to be sewn up and then the needle is released to manually form up a knotted seam per stitch during a suturing operation which leads to a long time and a physically heavy burden on the side of the operator as well as the patient. For shortening the suturing time there has been provided a structure shown in FIGS. 18-24 of the attached drawings. A curved needle 11 is detachably attached to a needle bar 12 at its determined position of the suturing machine, the curved needle being formed with a needle eye 11a at its end portion and with an oblong curved groove 11b extending from a half way of the curve on the outer circumference to the needle eye 11a. A needle thread 13 guided in the curved groove of the curved needle is crossed with a shuttle thread 15 connected to a shuttle 14 which draws a determined reciprocating lock with respect to the suturing machine.

The suturing according to such a device may be continuously carried out in the lock stitching manner by drawing out the needle thread 13 from a thread bobbin (not shown), passing through a guide hole 16a of a needle thread guide piece 16 fixed to the needle bar 12 and the needle eye 11a via the oblong curved groove 11b of the needle 11, and penetrating the curved needle 11 into the parts 17 and 18 to be sutured up by operating the suturing machine, then tensing the needle thread 13 between the needle eye 11a and a needle penetrated point 18a thus to form a crescent thread loop 13L together with the thread guided in the guide groove 11b, then reciprocating the shuttle 14 connecting the shuttle thread 15 to the thread loop so that the needle thread 13 is, as shown in FIG. 22, crossed with the shuttle thread 15, and drawing out the curved needle 11 from the penetrating side and then tightening the needle thread 13 and the shuttle thread 15.

However, according to this conventional manner, since the oblong curved groove 11b opens outwardly, the needle thread 13 slips out from the groove when the needle thread 13 is loosened at penetrating the needle into the part to be sutured up. As a result, the thread 13 is, as shown in FIG. 24, tensed in double between the needle eye 11a and the penetrated hole 18a, so that it is difficult to catch the thread loop 13L by the shuttle 14.

SUMMARY OF THE INVENTION

An object of the invention is to form a checking portion at the outer circumference of the curved needle so as to prevent the thread from slipping out from the oblong curved groove which extends from a half way of the curve on the outer circumference to the needle eye so that a crescent thread loop is guided together with the thread in the guide groove between the needle eye and the penetrated hole of the part to be sutured for catching the thread loop by the shuttle.

The novel features which are considered as characteristic for the invention are set forth in particular in the appended claims. The invention itself, however, both as to its construction and its method of operation, together with additional features and advantages thereof will be best understood from the following description of specific embodiments when read in connection with the accompanying drawings.

BRIEF DESCRIPTION OF THE DRAWINGS

FIG. 1 is a side view of a curved needle according to the invention;

FIG. 2 is a vertical cross section along length of the needle;

FIG. 3 is a cross section along line A—A of the curved needle shown in FIG. 1;

FIG. 4 is a cross section along line B—B of the same;

FIG. 5 is a cross section along line C—C of the same;

FIG. 6 is a cross section along line D—D of the same;

FIG. 7 is a cross section along line E—E of the same;

FIG. 8 is a cross section along line F—F of the same;

FIG. 9 is a cross section seen from an arrow G of FIG. 1;

FIG. 10 is an enlarged vertical cross section of a part near a needle hole;

FIG. 11 is a perspective view showing a suturing process;

FIGS. 12 to 14 show a second embodiment of the invention, where

FIG. 12 is an enlarged perspective view of the curved needle;

FIG. 13 is a view showing an outer circumferential side of the curved needle developed along the curve of the curved needle;

FIG. 14 is an enlarged cross section viewed from line B—B in FIG. 13;

FIG. 15 is a view corresponding to still that in FIG. 13, relating to another embodiment of the invention FIG. 16 is an enlarged cross section viewed from line C—C of FIG. 15;

FIG. 17 is a cross section showing a needle thread loop in the suturing process;

FIGS. 18-24 show embodiments of the prior art where

FIG. 18 is an enlarged view of the curved needle;

FIG. 19 is a view showing an outer circumferential side of the curved needle developed along the curve of the curved needle;

FIG. 20 is an enlarged view viewed from line A—A of FIG. 20;

FIG. 21 is a perspective view showing the suturing process;

FIG. 22 is a perspective view showing that the needle thread loop is crossed with the shuttle thread;

FIG. 23 is a cross sectional view showing a regular needle thread loop in the suturing process; and FIG. 24 is a cross sectional view showing an irregular needle thread loop in the suturing process.

DETAILED DESCRIPTION OF THE INVENTION

In reference to FIGS. 1 and 2, a suturing needle 1 is composed of a needle grip 1a to be held by a holding piece of a suturing machine, and a curved part 1b of the needle which is integrally formed with the needle grip, the needle being formed with a needle eye 1c nearly to the end point and being defined with a spot facing 1*d* extends along the outer circumference at the outside of the curve. The spot facing 1*d* is formed with a thread guide groove 1*e* for the needle thread 2 (FIG. 10) and the grip 1*a* is formed with a flat portion 1*f*. Although not being essential, in the present embodiment, the curved part 1*b* is formed with a cutting edge 1*g* spaced from the end point about ⅓ of an overall length of the suturing needle 1 to enable the needle to smoothly penetrate into a part to be sutured up and not to injure the human part. The cutting edge 1*g* is formed horizontally at a right angled cross section along the length of the suturing needle 1 and extended vertically toward the inside of the curved part 1*b*. The suturing needle has a triangular cross section as shown in FIG. 3 nealy a line A—A in FIG. 1, and a triangular cross section as shown in FIG. 5 nearly a line C—C in the same and a cross section as shown in FIG. 6 at a line D—D to smoothly merge into a circular cross section as shown in FIG. 7. The needle hole 1*c* is oblong as shown in FIG. 9 at the arrow G in FIG. 1, and the outer circumference is formed with a sufficient curvature at a vertical cross section of the curved part 1*b* so that the needle thread 2 passing in the eye is smoothly moved. The numeral 1*h* is a releasing part of the curved part, formed nearly the needle hole 1*c*.

A next reference will be made to actuation of the present invention. In FIG. 11, the suturing needle 1 is held at its grip 1*a* by a pair of holding pieces of the suturing machine, and spaced with respect to the suturing machine at a determined distance. When the suturing machine is made oblique and the suturing needle 1 is penetrated into the parts 4, 4' as shown in FIG. 11 the needle is smoothly penetrated while conveniently cutting the sutured parts 4, 4' with the cutting edge 1*g*. Under the penetration, the needle thread 2 is tensed in straight between the needle hold 1*c* and the penetrated hole 4*a'* of the part 4', and changes into a needle thread loop 2*a* of the crescent shape together with the thread guided in the thread guide groove 1*e*.

In the operation, it is improper to form a thread loop by utilizing the friction between the needle and the sutured part which is produced when the needle returns as is seen in the ordinary sewing machine, because the thread loop is deformed due to the adhesive blood and becomes difficult to be caught by a shuttle 5.

Then, the thread 6 connected to the shuttle is passed through the needle thread loop 2*a*, and the needle is drawn out from the penetrating side, and the needle thread 2 and the thread are tightened to form in succession stitchings.

A further reference will be made to a second embodiment in reference to FIGS. 12 to 17. In FIG. 12, the curved needle 111 is formed with the needle eye 111*a* at its end point and with the oblong curved groove 111*b* for guiding the thread from the half way of the outer circumferential part to the needle eye 111*a* on the outer circumference of the needle, and further provided with a checking portion 111*c* at a center part in the length thereof for preventing the thread from slipping out from the curved groove. The checking part 111*c* may be partially provided at the center of the curved groove 111*b* as shown in FIGS. 12 and 13, or may be formed with sufficient length as shown in FIG. 15. The checking parts 111*c* and 111*c'* can be formed by elastic deformation of walls 111*d*, 111*e* and 111*d'*, 111*e'* after processing the oblong curved grooves 111*b* and 111*b'*.

Actuation of the present invention as composed above will be explained. Prior to the suturing, when the needle thread 112 is drawn out from the bobbin (not shown) of the suturing machine, and passed through the guide hole 114*a* of the thread guide piece 114 attached to the needle holder 113 and the needle eye 111*a* by guiding along the oblong curved groove 111*b* of the curved needle 111 and, penetrated into the sutured parts 115 and 116 as shown in FIG. 17, the needle thread 112 is tightened between the needle eye 111*a* and the sutured piece 116*a*, and is changed into the needle thread loop 112L of the crescence together with the thread guided in the curved groove 111*b* by the checking portion 111*c*, to enable said loop to cross with the shuttle thread connected to the shuttle (not shown).

It will be understood that each of the elements described above, or two or more together, may also find a useful application in other types of suturing needles differing from the types described above.

While the invention has been illustrated and described as embodied in a suturing needle it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A suturing needle for use in medical operations, comprising a needle grip to be held by a suturing machine and an elongated curved portion formed with a needle eye to receive a needle thread, said curved portion having an outer surface and an inner surface of substantially circular shape, said outer surface being formed with an elongated thread guide groove for guiding the needle thread toward said needle eye, said elongated groove being provided with a checking portion formed as to partially close said groove to thereby prevent the needle thread from slipping out from said groove.

2. The needle of claim 1, having an end point, said needle eye being located in the vicinity of said end point.

3. The needle of claim 2, further including a cutting edge formed on said inner surface and located about ⅓ of an overall length of the needle from said end point.

4. The needle of claim 3, wherein said cutting edge is extended horizontally normal to the length of the needle and vertically toward said inner surface.

5. The needle of claim 1, wherein said outer surface has opposite walls bounding said groove, said checking portion being formed by elastic deformation of said walls.

* * * * *